US008911667B2

(12) United States Patent
Beumer et al.

(10) Patent No.: US 8,911,667 B2
(45) Date of Patent: Dec. 16, 2014

(54) DEVICE FOR PREPARING AND/OR TREATING A BIOLOGICAL SAMPLE

(75) Inventors: Tom Beumer, Oss (NL); Frederic Foucault, Amberieu en Bugey (FR); Emiliano Maione, Bagno a Ripoli (IT); Agnes Rubens, Montceaux (FR)

(73) Assignee: Biomerieux, Marcy l'Etoile (FR)

( * ) Notice: Subject to any disclaimer, the term of this patent is extended or adjusted under 35 U.S.C. 154(b) by 315 days.

(21) Appl. No.: 13/124,266

(22) PCT Filed: Nov. 4, 2009

(86) PCT No.: PCT/FR2009/052133
§ 371 (c)(1),
(2), (4) Date: Apr. 14, 2011

(87) PCT Pub. No.: WO2010/052429
PCT Pub. Date: May 14, 2010

(65) Prior Publication Data
US 2011/0200486 A1   Aug. 18, 2011

(30) Foreign Application Priority Data
Nov. 5, 2008   (FR) ...................................... 08 06169

(51) Int. Cl.
*G01N 33/48* (2006.01)
*G01N 35/00* (2006.01)
*B01L 3/00* (2006.01)
*B01L 3/02* (2006.01)
*B01L 9/00* (2006.01)

(52) U.S. Cl.
CPC ... *B01L 3/502715* (2013.01); *B01L 2200/0621* (2013.01); *B01L 2200/027* (2013.01); *B01L 2300/0822* (2013.01); *B01L 3/0293* (2013.01); *G01N 2035/00158* (2013.01); *G01N 35/00693* (2013.01); *B01L 2200/16* (2013.01); *B01L 9/527* (2013.01)
USPC ........................... 422/68.1; 422/502; 422/509

(58) Field of Classification Search
CPC .................. B01L 2200/027; B01L 2200/0621; B01L 2200/16; B01L 3/502715; B01L 9/527; G01N 2035/00158
USPC .......................................... 422/68.1, 502, 509
See application file for complete search history.

(56) References Cited

U.S. PATENT DOCUMENTS 5,290,521 A * 3/1994 DeStefano, Jr. ............... 422/563
6,374,684 B1   4/2002 Dority
6,440,725 B1   8/2002 Pourahmadi et al.
(Continued)

FOREIGN PATENT DOCUMENTS

GB   2 165 216 A   4/1986

OTHER PUBLICATIONS

International Search Report issued in International Application No. PCT/FR2009/052133 on Mar. 1, 2010 (with translation).

(Continued)

*Primary Examiner* — Paul Hyun
(74) *Attorney, Agent, or Firm* — Oliff PLC

(57) ABSTRACT

A device for preparing and/or treating a biological sample including an assembly of storage chambers and/or reaction chambers intended for receiving a fluid, the chambers being separated by walls so as to form an assembly of adjacent chambers. The device includes a base and a drawer including the assembly of adjacent chambers, the drawer being movable in relation to the base, the drawer including a contact surface connected to first means for establishing fluid communication connected to the inside of at least one chamber, the contact surface of the drawer being intended to be positioned facing a contact surface of the base including at least one position at which second means for fluid communication connected to detection means are placed.

21 Claims, 9 Drawing Sheets

(56) References Cited

U.S. PATENT DOCUMENTS

| | | |
|---|---|---|
| 6,534,008 B1 | 3/2003 | Angros |
| 6,878,540 B2 | 4/2005 | Pourahmadi et al. |
| 6,881,541 B2 | 4/2005 | Petersen et al. |
| 6,964,862 B2 | 11/2005 | Chen |
| 2001/0012612 A1 | 8/2001 | Petersen et al. |
| 2006/0275861 A1 | 12/2006 | Angros et al. |
| 2006/0292036 A1 | 12/2006 | Gould et al. |

OTHER PUBLICATIONS

Written Opinion of the International Searching Authority issued in International Application No. PCT/FR2009/052133 on Mar. 1, 2010 (with translation).

International Preliminary Report on Patentability issued in International Application No. PCT/FR2009/052133 on Jun. 7, 2011 (with translation).

\* cited by examiner

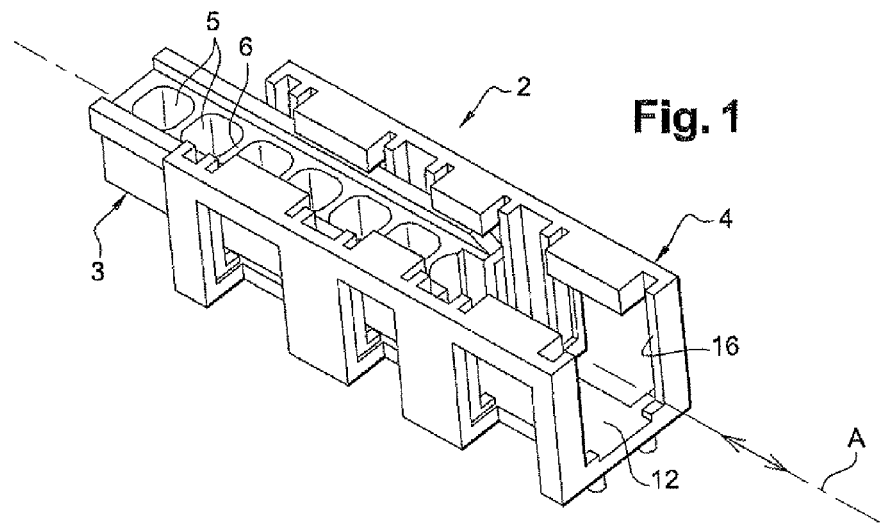
Fig. 1
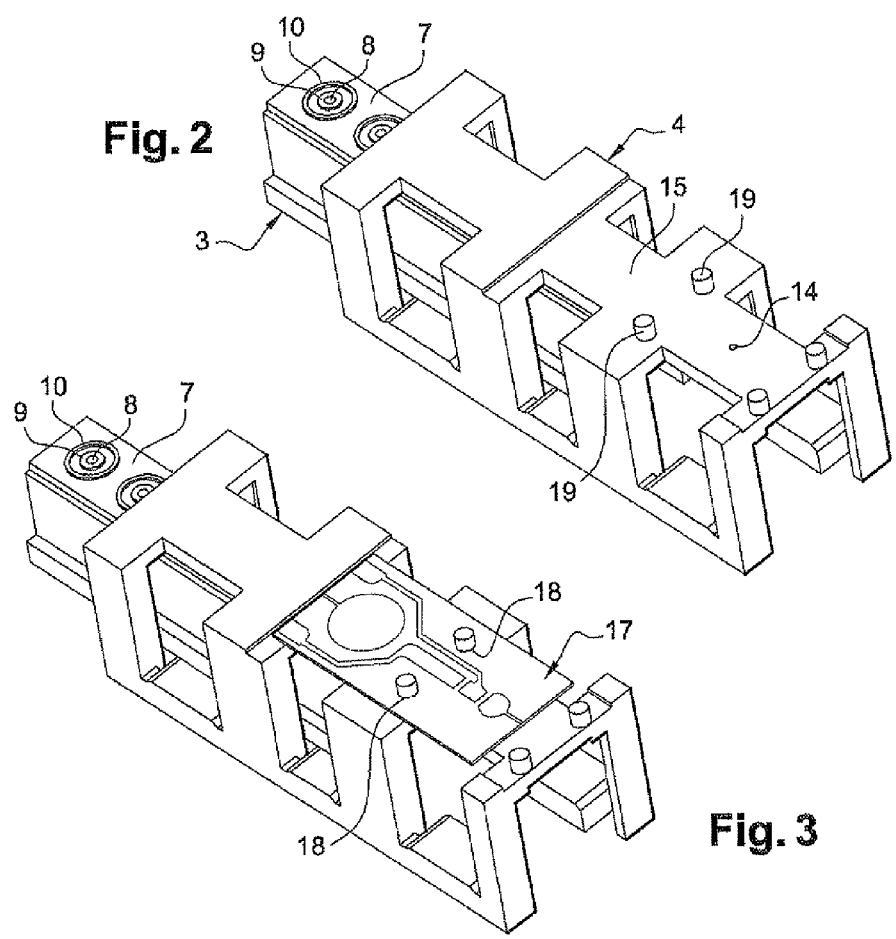
Fig. 2
Fig. 3

DEVICE FOR PREPARING AND/OR TREATING A BIOLOGICAL SAMPLE

This application is a national stage application of PCT/FR2009/052133 filed on Nov. 4, 2009, which claims the benefit of priority to FR 0806169 filed on Nov. 5, 2008, the disclosures of which are incorporated herein in their entirety.

The present invention relates to a device for preparing and/or treating a biological sample.

A device of this kind is intended notably to be used in the automation of biological protocols, notably of complex biological protocols.

As a nonlimiting example, said device can be applied in the detection of pathogens or of molecules, nucleic acids or proteins, of a pathogen.

Said biological protocol must preferably be carried out in a low-cost consumable device, which is connected to the detection module, and which is changed between each test. This consumable can be inserted in a treatment apparatus containing expensive components, for example mechanical or optical components.

Various techniques are used for automating complex biological protocols, such as immunoassay protocols, starting from a sample of a few milliliters. In all cases, the presence of several reagents requires the existence of various storage chambers and at least one reaction chamber. Means for moving the fluids are also necessary.

A first known device, used notably by the company Genpoint and employing a preparation robot marketed by the company Tecan, comprises means for moving, in three dimensions, a pipet and a plate having a plurality of wells, said wells containing either a reagent, or a sample.

The pipet is moved above the plate so as to be positioned in a well in order to take up a quantity of reagent, then it is positioned in the well containing the sample in order to deliver that quantity of reagent in said well, successively for each reagent.

Additional means necessary for the development of the reactions, in particular means for heating or for magnetic capture, can be arranged under the plate.

Such a device has the drawback that it uses precision mechanical means for moving the pipet, which have a complex structure and are difficult to transport.

To avoid contamination between tests, it has therefore been envisaged to perform unit tests in disposable sealed devices.

Thus, documents U.S. Pat. No. 6,878,540, U.S. Pat. No. 6,440,725 and U.S. Pat. No. 6,881,541 describe devices having a disposable cartridge comprising a set of chambers or reservoirs intended to receive notably a sample, fluids for washing and elution, reagents, the chambers or reservoirs being connected by a set of channels. These devices also comprise a microfluidic chip. The movement of the fluids between the various chambers and reservoirs is provided by means of the set of channels under the action of pumps and of flow control means of the type of valves or fluidic diodes. One of the uses of these devices is for carrying out the treatment of a fluidic sample for extracting and amplifying nucleic acids, notably by PCR.

For its part, document U.S. Pat. No. 6,734,684 also describes a disposable cartridge comprising a set of chambers and reservoirs. In the case of this document, a single treatment chamber is used, which can be put in fluid communication with other chambers or reservoirs selectively by means of channels provided in a rotating unit.

These solutions are effective in reducing contamination, but involve the provision of a structure for fluid communication between the chambers and for movement, which is still complex.

Document U.S. Pat. No. 6,964,862 describes a device comprising a disposable element having chambers separated by walls permitting fluid communication above a defined pressure. Each chamber is filled with a specific fluid prior to closure. Communication between the fluids contained in two adjacent chambers is secured by mechanical pressure on one of the two chambers, which causes an opening to appear in the separating wall.

This last-mentioned device makes it possible to simplify the provision of communication between the chambers, and also makes it possible to limit contamination between tests.

With miniaturization of the aforementioned devices, the amounts of liquids used have smaller and smaller volumes. These amounts are becoming so small that it is now difficult to use disposable containers with integrated reagents. In fact, on cost grounds, the materials used for making the chambers or reservoirs are produced from cheap, basic plastics, such as polyolefins. These materials do not provide long-term hermeticity and have poor barrier properties unless suitably treated. Thus, diffusion may take place through the walls. This leads notably to changes in concentration of the reagents due to evaporation of the solvent. Such evaporation can be ignored in the case of quantities of several hundred μl, but cannot be ignored for volumes of reagents of less than 50 μl.

This means that the reagents ought not to be placed in the device until just before their use.

With miniaturization of the aforementioned devices, the devices themselves are getting smaller. It can be estimated that the size limit permitting easy manipulation is of the order of a postage stamp or of a sugar lump. An operator cannot assemble or manipulate elements of this size, in view of the time it would take for each operation and the risk of losing parts of the device. It is more practical to use sets of disposable devices comprising up to several hundred devices. Automatic apparatus will take care of manipulation of the disposable, single-use devices.

Finally it should be noted that the devices are assembled from several elements received from different manufacturers. Therefore the structure of these devices should be made suitable for assembly which must be automated, in view of the tolerances imposed, which are of the order of about ten μm.

It is therefore desirable to provide a small device that can easily be filled and used by an automatic apparatus. This apparatus must also be of low cost, easy to manufacture, while offering satisfactory performance.

The present invention aims to solve some or all of the drawbacks mentioned above.

With this objective, the present invention relates to a device for preparing, for treating and/or for analyzing a biological sample comprising a base and a drawer, movable in translation relative to the base, comprising a set of storage chambers and/or reaction chambers intended to receive a fluid, the chambers being separated by walls so as to constitute a set of adjacent chambers, the drawer comprising moreover a contact surface onto which first means for establishing fluid communication open, connected to the internal volume of the chambers, the contact surface of the drawer being positioned facing a contact surface of the base comprising at least one position at which second fluid communication means, connected to detection means, are arranged.

To effect a transfer of fluid between the chambers of the drawer and the detection means, the first fluid communication means of a chamber must be aligned with the second fluid communication means of the contact surface of the base. It is thus possible to move the drawer so that different chambers of the drawer are brought into communication with the detection means alternatively, at each stage transferring a defined quantity of fluid between the chamber and the detection module.

These arrangements permit simple and robust execution of complex biological protocols. They make it possible to deliver very small amounts of liquids, even if the latter have high wettability, without leaks or contamination.

Preferably, the device according to the invention comprises at least one sealing means provided on the contact surface of the drawer.

Advantageously, the detection means comprise a fluidic channel and/or a reaction chamber connected to the second fluid communication means.

Preferably, the detection means comprise a microfluidic chip mounted on the base and containing a fluidic channel.

Advantageously, the first fluid communication means comprise at least one opening made in the drawer and opening onto the contact surface of the drawer.

Preferably, the sealing means comprise at least one seal positioned around the opening. More preferably, the sealing means comprise two concentric seals, positioned around the opening.

According to an advantageous embodiment, the device according to the invention further comprises wipers that are intended to be positioned between the contact surface of the drawer and the contact surface of the base.

Preferably, the device comprises mechanical means for positioning the microfluidic chip on the base. Said positioning means can comprise at least one pin and an opening of complementary shape.

Advantageously, the drawer comprises two parts constituted of two different materials, one of said parts comprising a material that is more rigid than that of the second part, the second part bearing the first fluid communication means.

Preferably, the base comprises a housing, the section of which is able to guide the movement of the drawer. The dimensions of the drawer can in particular be greater than those of the housing, so as to create a stress when the drawer is placed in the housing and to keep the contact surface of the drawer in contact with the contact surface of the base. The base and the drawer are notably arranged to permit a relative movement of translation of the drawer relative to the base.

According to one embodiment, the drawer comprises a separate set of positioning stops or notches depending on its direction of movement relative to the base.

Advantageously, the microfluidic chip and the base are formed in the same piece, the upper face of the chip at least partly constituting the contact surface of the base.

The present invention also relates to an apparatus for analysis comprising a device as described previously, and having, at a treatment station, means for driving the movement of the drawer relative to the base, and means arranged for transferring an amount of fluid to a chamber of the drawer or from a chamber of the drawer via the fluid communication means.

Advantageously, the apparatus comprises, at the treatment station, electrical connection means comprising at least one conducting tab intended to establish electrical connection with a contact of the microfluidic chip of the device according to the invention.

According to advantageous embodiments, the apparatus can comprise:
 a station for storage of a set of devices, and/or
 a station for filling the chambers of the drawer with reagents, liquids and/or samples.

Preferably, the storage station comprises storage means intended to receive a set of devices stored on a set of columns and rows.

Advantageously, the apparatus comprises, at the filling station, at least one pipet or a needle for filling the chambers of a drawer that can move between a first high position and a second low position of filling of a chamber of a drawer, said needle or pipet being connected to a reservoir of reagent or some other liquid, or to the container of a sample to be analyzed.

Preferably, the apparatus comprises conveying and/or manipulating means for moving the devices between the stations of the apparatus.

The invention will be better understood from the detailed description that is presented below, referring to the appended drawings in which:

FIG. 1 is a perspective view of a first device according to the invention seen from above.

FIG. 2 is a view of the device of FIG. 1 seen from below, without the microfluidic chip.

FIG. 3 is a view of the device of FIG. 1 seen from below, with a microfluidic chip mounted on the base of the device.

In the following detailed description of the figures defined above, the same elements or the elements fulfilling identical functions will keep the same references so as to make the invention easier to understand.

Figure 4:
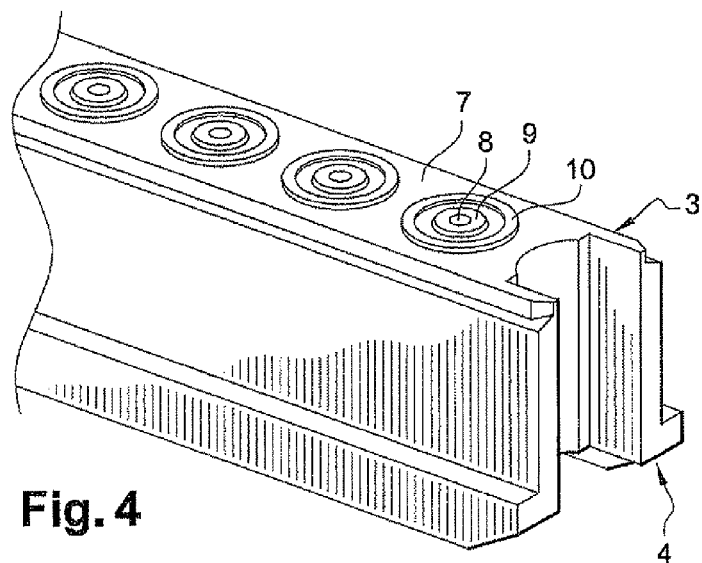
FIG. 4 is a perspective view on an enlarged scale of the bottom of a first drawer that can be used in the device of FIG. 1.

As shown in FIGS. 1 to 3, according to a first embodiment of the invention, a device 2 for preparing and/or treating a biological sample has a drawer 3 comprising a set of storage chambers 5 and/or adjacent reaction chambers, separated by walls 6 and intended to receive a fluid. The device 2 further comprises a base 4, relative to which drawer 3 can be moved.

The chambers 5 are aligned in a direction A and drawer 3 is movable in translation in this same direction A relative to the base 4. Each chamber 5 is open on an upper face of the drawer 3.

The drawer 3 comprises a lower contact surface 7 onto which first means for establishing fluid communication open, connected to the volume of at least one chamber, comprising a communicating opening 8 in the bottom of each chamber 5.

A first circular seal 9 is provided on the contact surface 7 of the drawer 3 around the communicating opening 8. A second seal 10 concentric with the first seal 9 is provided on the contact surface 7 of the drawer 3 on the outside of the first seal 9. This arrangement maintains good hermeticity even if the first seal is damaged.

The contact surface 7 of the drawer is positioned facing a contact surface 12 of the base 4 comprising at least one position at which second fluid communication means are arranged, complementary to the first fluid communication means of the drawer, constituted of a communicating channel extending between a first opening 13 in the contact surface 12 of the base 4 and a second opening 14 situated on a lower face 15 of the base 4.

Thus, seal 9 is able to ensure hermeticity of each chamber by establishing hermeticity around opening 8 by bearing against the contact surface 12 of the base when this opening is not opposite opening 13, and permits fluid communication without leakage between opening 8 and opening 13 when these openings are opposite one another.

The base 4 comprises a housing 16 whose section is able to guide drawer 3 in translation. The dimensions of drawer 3 are, however, slightly greater than those of housing 16, so as to create a stress when drawer 3 is received in housing 16 and to maintain the lower contact surface 7 of drawer 3 in contact with the contact surface 12 of the housing and thus ensure good hermeticity of the seals 9, 10 which are pressed against the contact surface 7 of the base 4.

A microfluidic chip 17 containing a fluidic channel 21 is mounted on the base, so that the second opening 14 of the channel provided in base 4 is arranged opposite an inlet hole of the microfluidic chip.

Regarding the structure and manufacture of this chip, these will not be described here. Various types of chips can be used. As reference, we may cite documents WO 98/23957 and EP1255690, which describe the structure and manufacture of these types of chips. Of course, types of microfluidic chips other than those described in these documents can be used in device 2.

The base 4 and the chip 17 comprise mechanical means for positioning the microfluidic chip on the lower face of the base constituted of two through-openings 18 made in the chip and two pins 19 provided on the lower face 15 of the base 4 intended to be housed in the two openings 18 of chip 17, the pins 19 and openings 18 having complementary shapes, in this case a circular shape.

The chip 17 is advantageously fixed by gluing on the lower face 15 of the base 4.

The chip 17 comprises, as well as an inlet for liquid, an outlet for liquid, which can be positioned on the top or on the bottom of the chip depending on the embodiment.

To effect a transfer of fluid between the chambers 5 and the chip 17, the opening for fluid communication 8 of a chamber 5 must be aligned with the opening 13 made in the contact surface 12 of the base 4. It is thus possible to use driving means that we shall describe later in order to push the drawer so as to align a first opening of a first chamber of the drawer opposite the opening in the base. When the fluid contained in the corresponding chamber is transferred, the driving means push the drawer so as to align the opening of a second chamber of the drawer opposite the opening in the base, to transfer the fluid contained in this second chamber, and then to repeat these operations up to the last chamber.

The base 4 can be fabricated by injection molding, notably from a single material. Various materials can be used for the base 4, and should preferably have the following properties:
good flatness, i.e. absence of excessive contraction or of deformation during ejection of the molding from the mold;
a smooth surface;
good mechanical strength for holding the drawer firmly against the contact surface of the base.

The position of the point of injection must be selected so as to permit flatness and satisfactory filling. Moreover, the design of the base must take into account the deformation under the stress due to fitting of the drawer. The base 4 can be made for example of polycarbonate (PC), polystyrene (PS), polymethyl methacrylate (PMMA), polyether imide (PEI), polyethylene terephthalate (PET), polyethylene naphthalate (PEN), acrylonitrile-butadiene-styrene (ABS), styrene-acrylonitrile (SAN).

The drawer 3 is also a plastic injection molding which can be produced in two different ways, with single injection or double injection of two different materials.

Single injection is simpler and less expensive, whereas double injection can improve the robustness of the assembly.

Drawer 3, fabricated from a single material, can be made from different polymers, such as notably thermoplastic polymers or thermoplastic elastomers.

Drawer 3, as shown in FIGS. 1 to 4, is made from a single material, which can of course simplify its manufacture.

Figure 5:
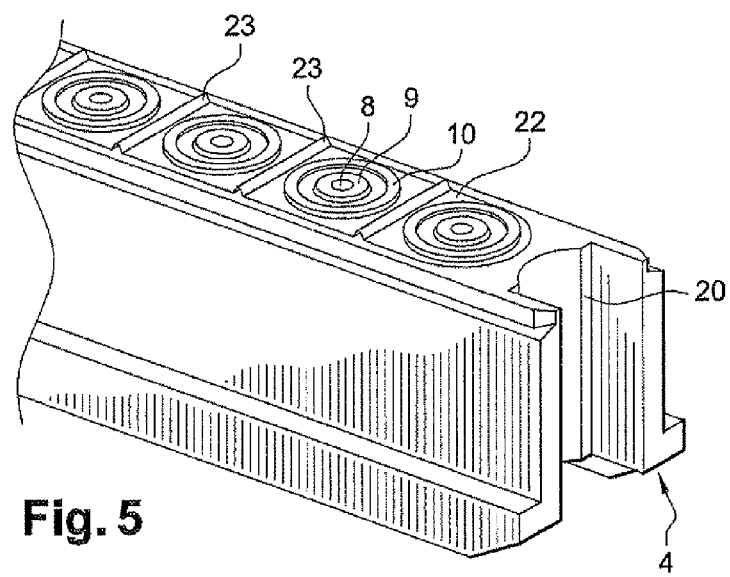
FIG. 5 is a perspective view on an enlarged scale of the bottom of a second drawer that can be used in the device of FIG. 1.
Figure 6:
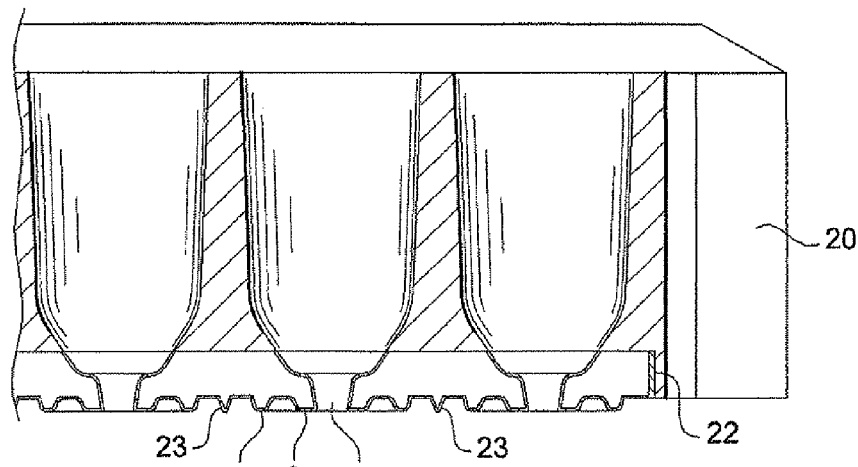
FIG. 6 is a side view of the drawer of FIG. 5.

According to one embodiment of drawer 3 shown in FIGS. 5 and 6, the drawer comprises two parts 20, 22 constituted of two different materials, part 20 comprising a material that is more rigid than that of part 22, the latter having the fluid communication means 8 and the sealing means 9 and 10.

This drawer can be produced by injection of two materials, a first material that is more pliable being used for part 22 which is intended to provide hermetic contact with the base, notably a thermoplastic elastomer or a polyolefin, and a strong, inexpensive polymer for part 20 constituting the rest of the drawer, for example a thermoplastic polymer, which can be a polyolefin. The adhesion of these two polymers must be satisfactory to prevent leaks or disassembly of the two materials.

Similarly to what has been described for the first embodiment of the drawer, the contact zone of the drawer comprises two concentric seals 9, 10 around the opening 8.

Between two openings of two chambers, the contact surface can also have a wiper 23.

The wipers 23 are made in the form of a projecting portion of triangular, rectangular or semicircular profile.

The wipers 23 preferably have a height greater than that of seals 9, 10 and are intended to bear against the contact surface 12 of the base 4.

The effect of these wipers 23 is to scrape the residues situated between the contact surfaces 12 of the base and the contact surface 7 of the drawer outside of the two seals 9, 10 to confine these residues in a space contained between two successive wipers 23 so as to avoid contamination of the liquid contained in the other chambers 5 via the openings 8.

According to a second embodiment shown in FIGS. 7 to 12, the device 2 comprises, similarly to what was described in the first embodiment, a drawer 3, a base 4 and a chip 17 fixed under the base 4.

The base 4 has, on its contact surface 12 with the drawer 4, an opening permitting communication with the inlet of the channel of the microfluidic chip.

The base 4 also comprises a second through-channel, which communicates on the lower face of the base with the fluid outlet of the chip, and opens onto the upper face of the base at an outlet hole 24, at a projecting part 25 relative to the contact surface 12 with drawer 3.

Figure 7:
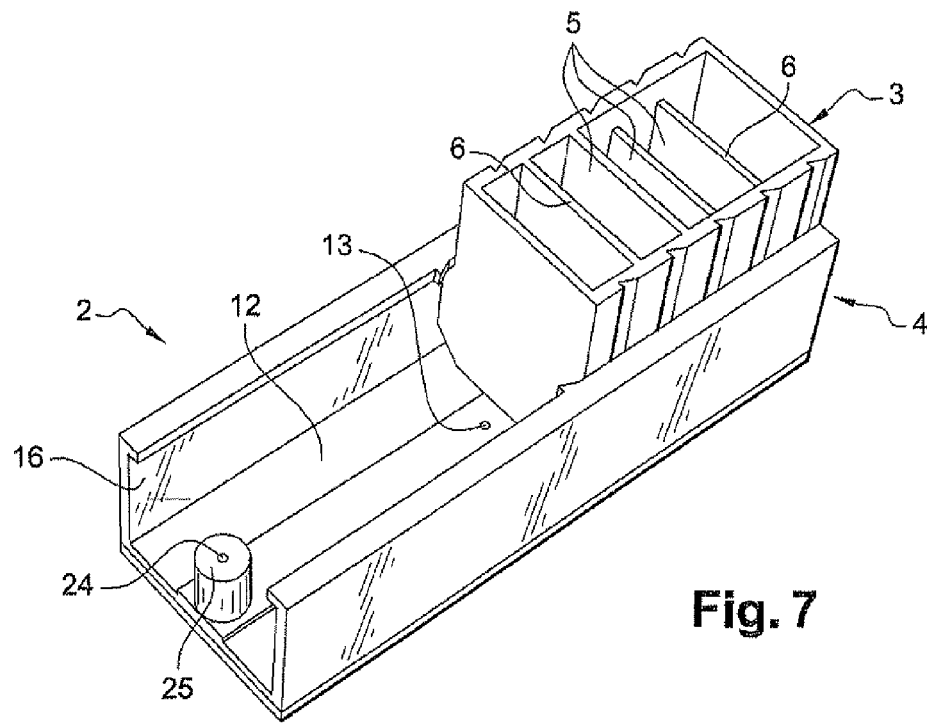
FIG. 7 is a perspective view of a second device according to the invention.
Figure 9:
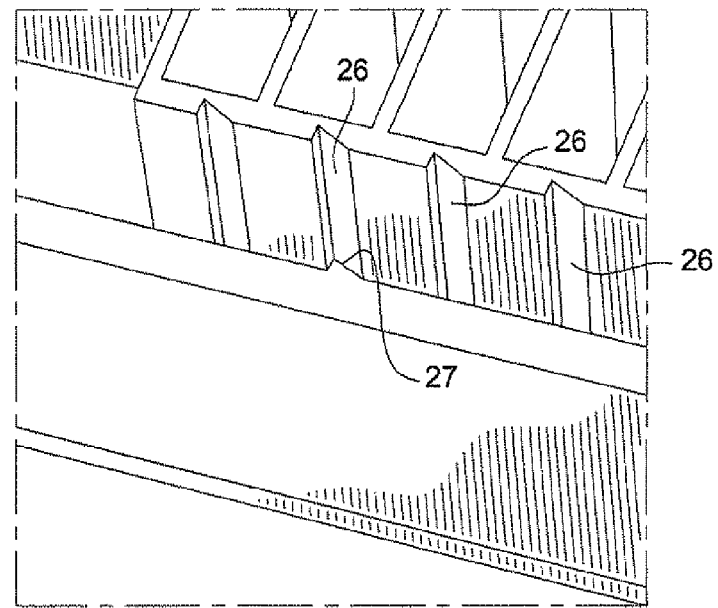
FIG. 9 is a detail view of the device of FIG. 8.

It should be noted that in this embodiment the lateral faces of the drawer have a set of positioning notches 26 that are intended to interact with a catch 27 positioned on a wall of housing 16 of the base 4, which can be seen notably in FIGS. 7 and 9. Advantageously, catches are positioned on both sides of housing 16 and notches 26 are positioned on both sides of drawer 3. This arrangement permits reliable definition of the positions in the movement of the drawer relative to the base at which a fluid communication opening 8 of a chamber 5 is opposite opening 13 of the base 4 communicating with the inlet of the chip 17.

Figure 8:
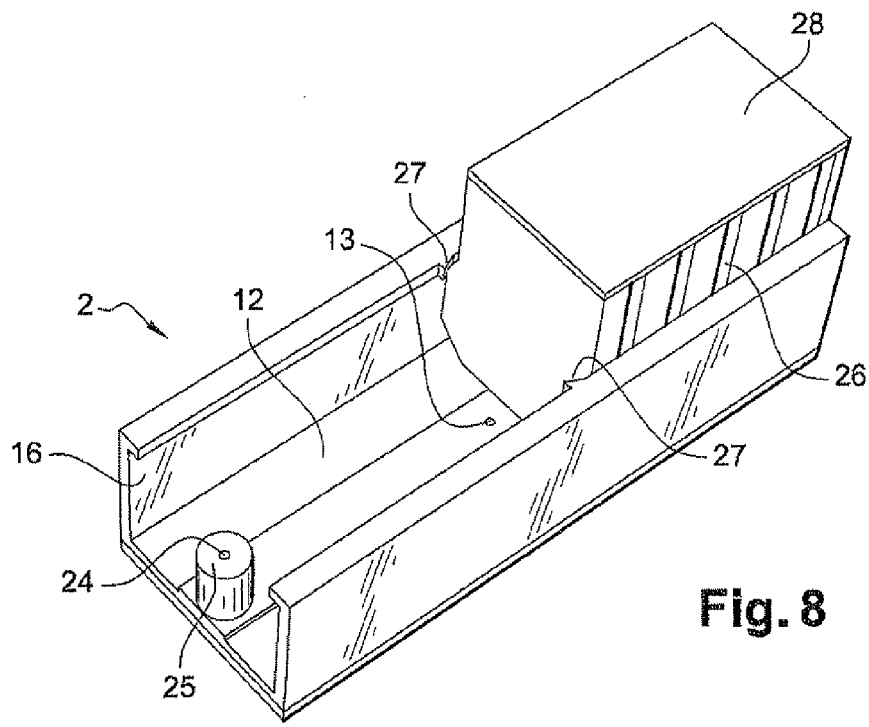
FIG. 8 is a perspective view of the device of FIG. 7 with a protective film positioned on the drawer.

It should be noted that, as shown in FIG. 8, the chambers are open on their upper faces and can be covered with a film 28 before use.

According to a variant that is not shown, chip 17 can be positioned directly in contact with the drawer, notably in a housing made in the contact surface of the base 4. This arrangement makes it possible to avoid contamination.

According to another variant that is not shown, chip 17 and the base may only constitute one and the same piece, obtained by injection molding. The upper face of the chip then partly constitutes the contact surface of the base.

A device according to the invention is intended to be used in an apparatus for analysis. Said apparatus for analysis comprises a station 30 for storing a set of devices 2, a station 32 for filling the chambers 5 of the drawer 3 with various reagents, liquids and samples and a treatment station 33.

Figure 13:
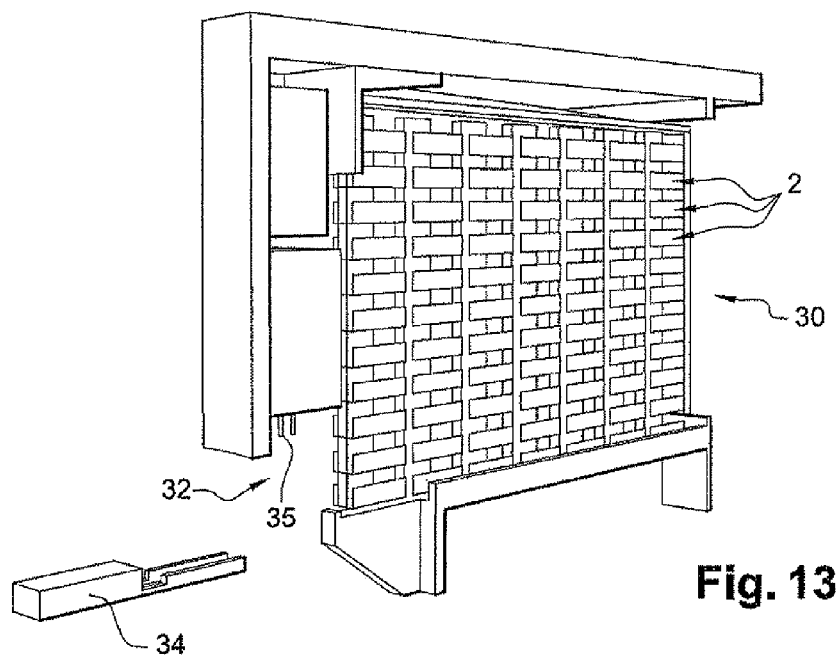
FIGS. 13 and 14 show a station for storage of devices and a station for filling of devices of an apparatus for analysis.
Figure 14:
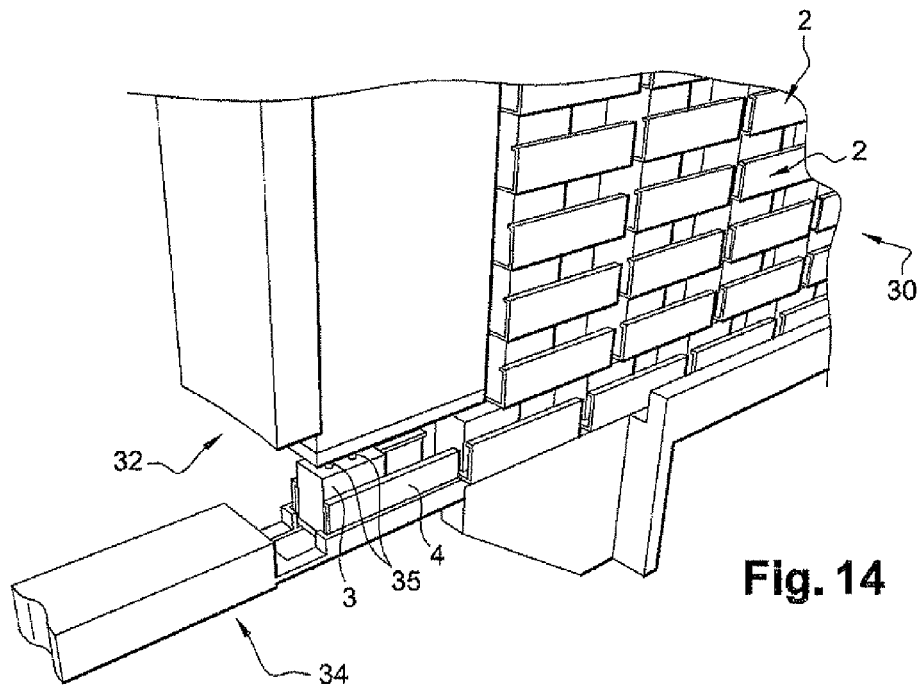

FIGS. 13 and 14 show a device storage station 30 and a device filling station 32.

The storage station 30 can receive a set of devices 2 stored on a set of columns and rows. A conveying device 34 makes it possible to take a device from this set and position it at the filling station 32.

This filling station 32 comprises a set of pipets or needles 35 for filling the chambers of the drawer. The needles 35 or pipets are movable so that they can pass from a high first position to a low second position for filling in a chamber 5 of a drawer 3.

Each needle 35 or pipet is connected to a reservoir of reagent or some other liquid, or to the container of a sample to be analyzed.

Once the chambers of the drawer have been filled, the device is carried into the treatment section by a manipulator 36 which takes the filled device 2 from the conveying means 34.

Figure 10:
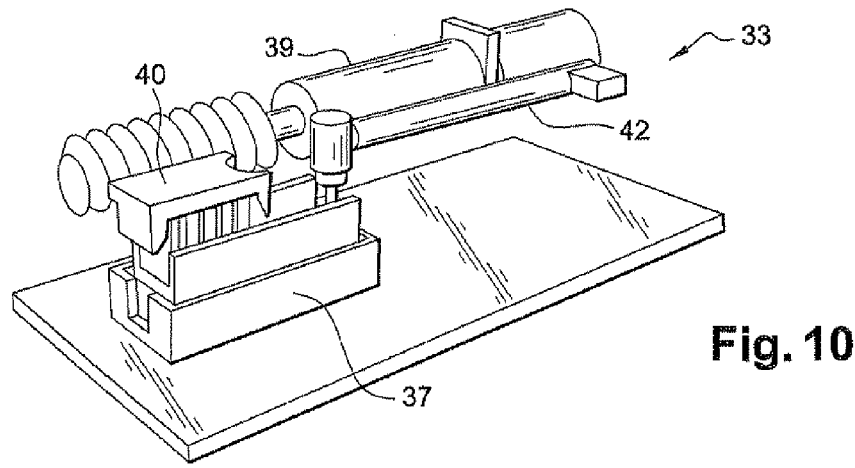
FIG. 10 is a view of a device of FIG. 7 positioned in an apparatus for analysis shown partially.
Figure 11:
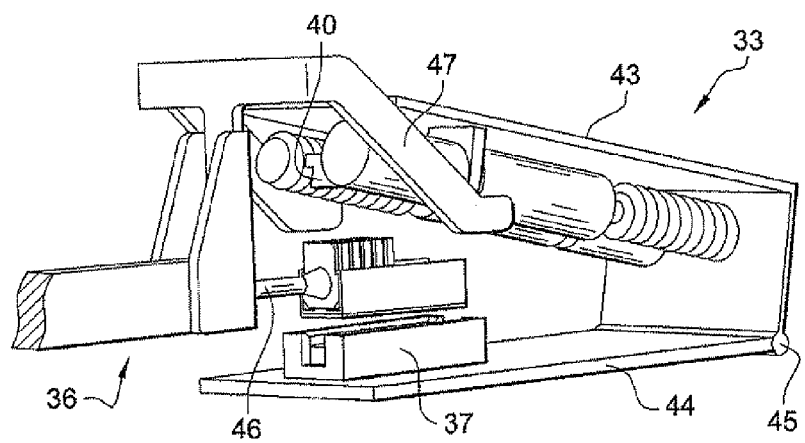
FIG. 11 is a view of a device of FIG. 7 positioned in an apparatus for analysis shown partially during a phase of installation of the device in the apparatus.
Figure 12:
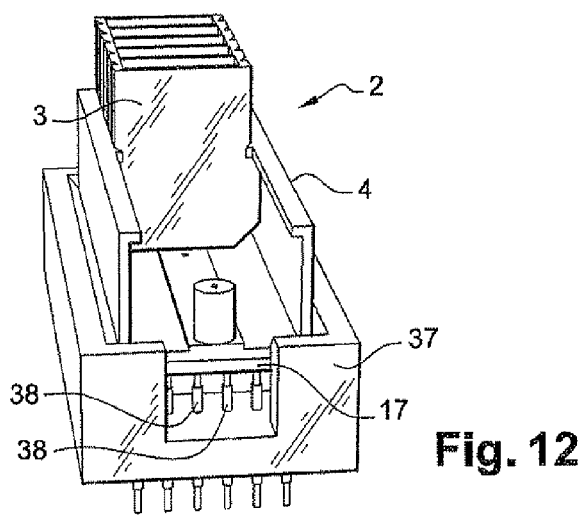
FIG. 12 is a front view of a device of FIG. 7 positioned in the receiving position of an apparatus for analysis.

In particular, as shown in FIGS. 10 to 12, the treatment station 33 of the apparatus for analysis comprises a receiving position 37 having a shape complementary to the shape of the base 4 of a device 2 in order to permit reliable positioning of said base 4. As shown in FIG. 12, the receiving position 37 is equipped with means for connection to the microfluidic chip, constituted of a set of conducting tabs 38 for establishing electrical connection with contacts of chip 17, said contacts being connected to the electrodes of the latter.

A spring acts upon the conducting tabs 38 to ensure that electrical contact is maintained.

The treatment station 33 comprises driving means for relative movement of the drawer relative to the base, said driving means comprising a motor 39 that moves a gripping mechanism 40 of the drawer 3. Advantageously, the gripping mechanism 40 interacts with the upper part of the drawer above the housing 16 in base 4.

As shown in FIGS. 10 and 11, the gripping mechanism is constructed in the form of a cover 40 that is intended to cover the drawer of a device 2 to interact with its walls and move said drawer 3.

The motor 39 has an outlet shaft comprising an endless screw interacting with notches or a thread of the cover 40 in order to move the cover in translation.

The motor 39 can be of the stepping type.

The gripping mechanism or cover 40 can also exert pressure on the device so as to hold the latter in position against the receiving position and against the means of electrical connection.

According to one embodiment, said pressure could be exerted by other mechanisms on the base 4 or the drawer 3.

The treatment station 33 also comprises a pump 42 connected to the outlet hole 24 of the base communicating with the outlet of chip 17. This pump 42 is therefore positioned downstream of the channel of chip 17 in the direction of the aspiration generated by the pump, the chambers of the device being arranged upstream of this channel.

The driving means 39, 40 of drawer 3 and the pump 42 are mounted on a first part 43 supporting the apparatus, movable relative to a second part 44 supporting the apparatus, on which the receiving position 37 of device 2 is mounted. These two supporting parts are in particular connected by a swivel linkage 45 with horizontal axis.

A device 2 can be positioned in the receiving position by the manipulator 36.

The manipulator 36 comprises means 46 for gripping a device 2 constituted for example of suction means intended to hold the device in position by the sucker effect on a front face of the drawer 3. The manipulator 36 also comprises a ramp 47 intended to interact with the first part 43 of the support.

During installation of a device, ramp 47 interacts with the first part 43 of the support, to raise the latter and move it away from the second part 44 of the support in order to release the receiving position of the device.

The manipulator 36 deposits the device at the receiving position 37 and is then withdrawn, the first part 43 of the support returning to its initial position, with cover 40 covering the drawer of the device 2 that has just been installed, and pump 42 coming into contact with the outlet hole 24 of the base 3.

Figure 15:
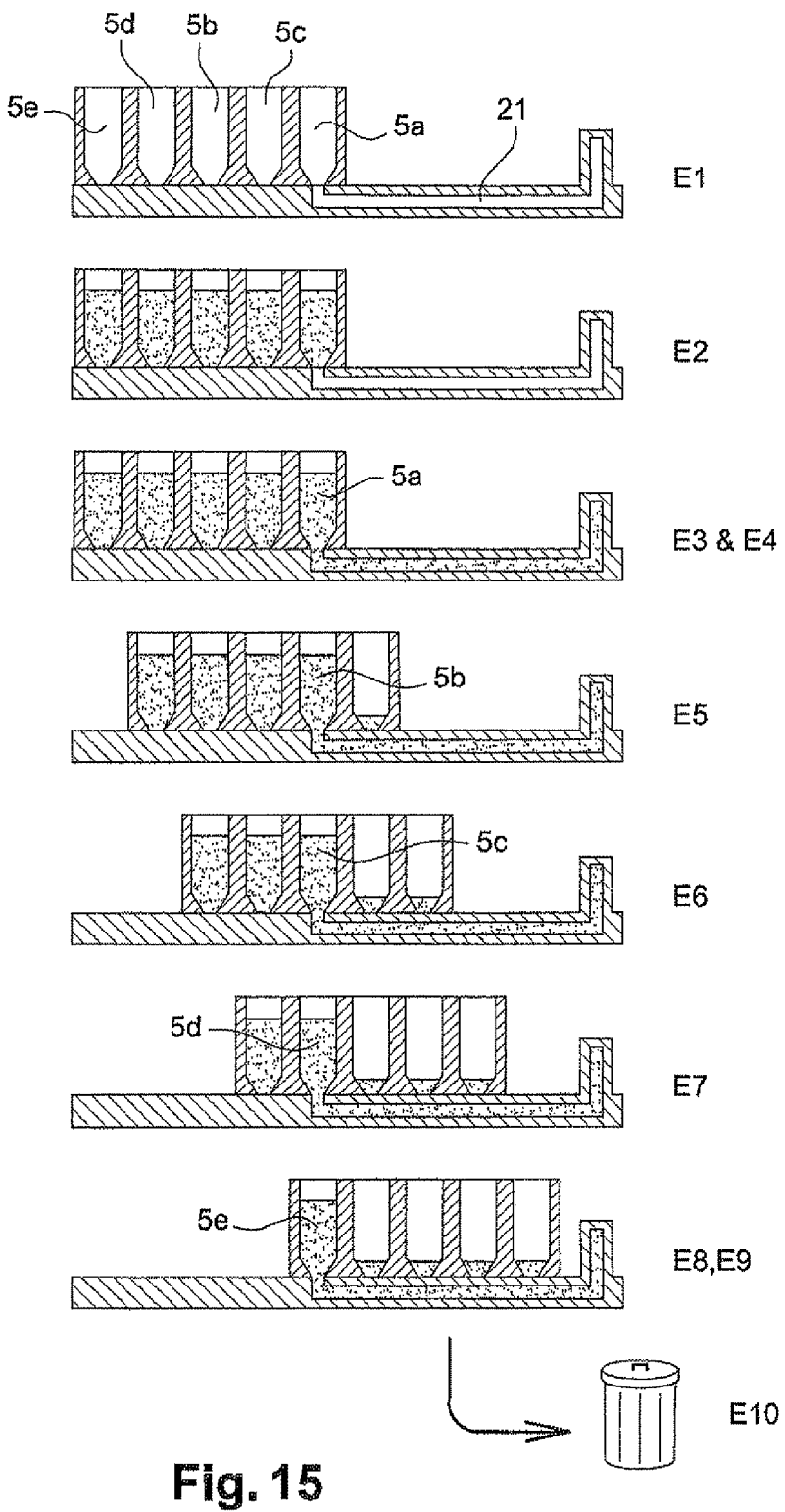
FIG. 15 is a flowchart showing different stages in the use of said device.

As shown schematically in FIG. 15, the combined operation of the apparatus for analysis and of a device according to the invention can be illustrated by the following stages for a device whose drawer 3 comprises five chambers $5a$, $5b$, $5c$, $5d$, $5e$.

In a first stage E1, a new device 2 is extracted from a set of devices stored in storage station 30 of the apparatus by conveying means 34 and is positioned at the filling station 32.

In a second stage E2, the chambers $5a$, $5b$, $5c$, $5d$, $5e$ are filled respectively with a prewetting buffer, the sample, the solution of conjugate, a washing buffer and a specific substrate for the analysis to be performed.

In a third stage E3, the device thus filled is transferred to the treatment station 33 of the apparatus.

In a fourth stage E4, the driving means move the drawer 3 until the first chamber $5a$ is connected to the chip, the pump aspirating the prewetting buffer from the first chamber into channel 21.

In a fifth stage E5, the driving means move the drawer until the second chamber 5b is connected to the chip, the pump aspirating the sample contained in the second chamber into channel 21.

In a sixth stage E6, the driving means move the drawer until the third chamber 5c is connected to the chip, the pump aspirating the conjugate contained in the third chamber into channel 21.

In a seventh stage E7, the driving means move the drawer until the fourth chamber 5d is connected to the chip, the pump aspirating the washing liquid contained in the fourth chamber into channel 21.

In an eighth stage E8, the driving means move the drawer until the fifth chamber 5e is connected to the chip, the pump aspirating the substrate contained in the fifth chamber into channel 21.

In a ninth stage E9, the aspiration of the pump is stopped, and detection of the signal in the chip is performed.

In a tenth stage E10, all of the fluids are led to a storage volume intended to receive wastes. In particular, it is possible for the pump to return all of the liquid to the device in one and the same chamber, and an overflow passage can be provided in the latter in order to fill the adjacent chambers, as shown in FIG. 7. As an alternative, this volume can be salted-out between each stage or at the end of the last stage in a waste storage volume by means of a three-way valve.

It should be noted that according to one embodiment of the invention, the sample and the solution of conjugate can be distributed in the same chamber, in this case chamber 5b. According to this embodiment, only chambers 5a to 5d are then filled.

According to another embodiment, in view of the very small volume of liquids used, it is possible to dispense with washing liquid. It is then the solution of substrate that performs the role of washing buffer. In this case, the solution of substrate is then distributed in chambers 5c or 5d, depending on whether the sample and the solution of conjugate are mixed or separate.

EXAMPLES

In the following examples, the device used comprises a drawer of the bi-material type and a base of polycarbonate (grade HPS1 marketed by the company SABIC).

The chip is glued onto the base with UV adhesive. The chips are of the type comprising a fluid inlet on their upper face, and an outlet on their lower face. These chips were supplied by the company Dyconex and have the following characteristics: an internal fluidic channel with width of 180 μm, depth of 35 μm, 24 working electrodes being arranged in the channel, with diameter of 50 μm and spacing of 150 μm.

Example 1

Assay of Troponin

A channel of a chip 17 is functionalized by adsorption of anti-troponin antibody at a concentration of 10 μg/ml, and is then dried under vacuum after passivation. The chip 17 is then assembled by UV gluing under the base 4. The drawer 3 is finally inserted in the housing 16 of the base 4.

The chambers 5 of the drawer are filled with 20 μl of the following reagents:
Chamber 5a: prewetting buffer,
Chamber 5b: the patient's serum or blood diluted to ½ with a solution comprising anti-troponin antibodies labeled with alkaline phosphatase (PAL),
Chamber 5c: para-aminophenyl phosphate (PAPP).

The device 2 constituted of the base 3, chip 17 and drawer 4 is then put in position in the apparatus and the assay protocol is initiated. The driving means 39, 40 of the drawer 4 are able to move the latter relative to the inlet of the channel 21 in order to dispense each of the reagents in the channel at the required time. The various reagents are aspirated from the chambers into the channel by means of a syringe pump. The volume of the syringe body is sufficient for each of the stages of the immunological test. This volume can be salted-out between each stage into a waste storage volume by means of a three-way valve.

The different stages of the immunological test are as follows:
stage 1: activation of the channel by a specific buffer (30 s)
stage 2: aspiration of the sample+conjugate mixture (5 min)
stage 3: aspiration of the substrate, which also serves as washing stage (1 min)

Figure 16:
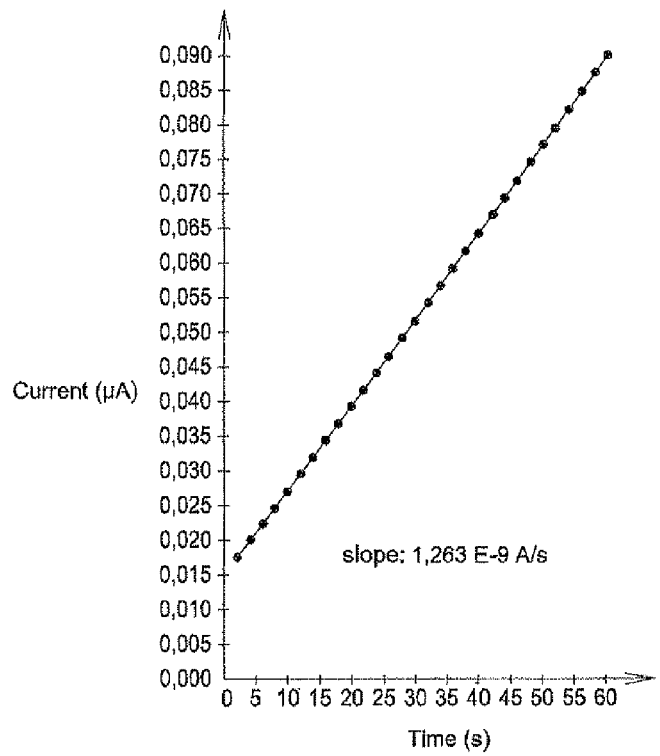
FIG. 16 is a curve relating to the first example showing the resultant current, which is due to oxidation of para-aminophenol, the product of degradation of PAPP in the presence of PAL as a function of time.
Figure 17:
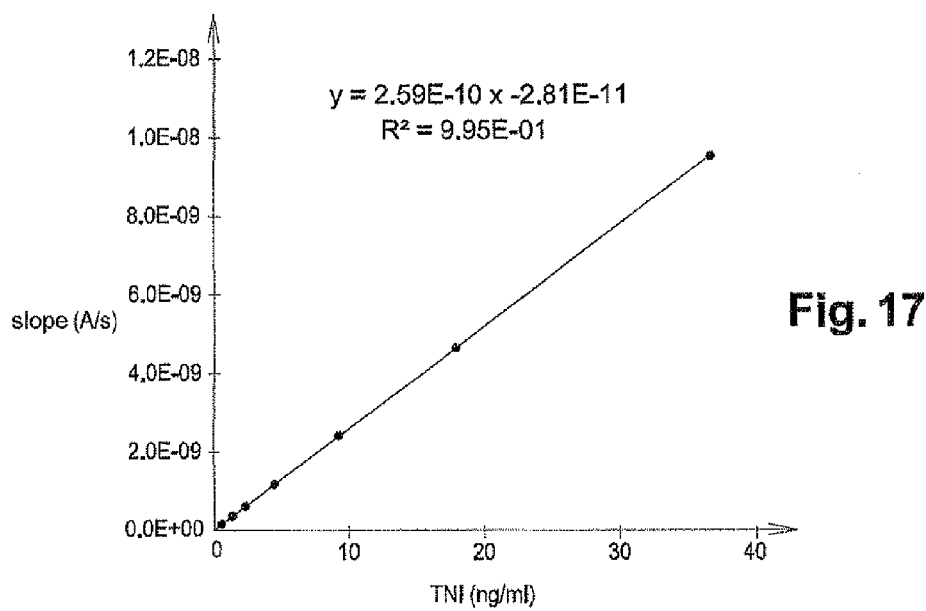
FIG. 17 is a curve relating to the first example showing the variation of the slopes of the current as a function of the known concentration of troponin in calibration sera.

At the end of these three stages, electrochemical detection is initiated. 30 cycles of gap potential (−0.2V/0.2V, 1 s at each potential) are applied. The resultant current, which is due to oxidation of the para-aminophenol, the product of degradation of PAPP in the presence of PAL, is measured. The variation of this current as a function of time is then plotted, and the slope at the origin of this kinetic curve is measured as shown in FIG. 16. This value is characteristic of the troponin concentration in the patient's sample. It can be used for determining the dose of the latter after establishing a calibration curve describing the variation of the slopes I=f(t) as a function of the known troponin concentration of calibration sera, as shown in FIG. 17.

Example 2

Simultaneous Assay of 4 Different Parameters

In this example, four channels 21 of four chips 17 are functionalized with different reagents specific for four separate analytes.

The first channel is functionalized with anti-troponin antibodies. The second channel is functionalized with anti-TSH antibodies. The third channel is functionalized with anti-estradiol antibodies. Finally the last channel is functionalized with toxoplasmosis antigens in order to detect immunity to toxoplasmosis. These four channels are put in place by gluing under four different bases, then four drawers are installed in each of the bases.

Table I below describes the reagents deposited for each of the chambers of the four drawers.

TABLE I

| Chamber of the drawer | 1 Troponin | 2 TSH | 3 Estradiol | 4 Toxoplasmosis |
| --- | --- | --- | --- | --- |
| Chamber 5a | Prewetting buffer | Prewetting buffer | Prewetting buffer | Prewetting buffer |
| Chamber 5b | Sample + conjugate PAL antibody | Sample | Sample + conjugate PAL antigen | Sample |
| Chamber 5c | Substrate | Conjugate PAL antibody | Substrate | Conjugate PAL antibody |
| Chamber 5d | | Substrate | | Substrate |

Figure 18:
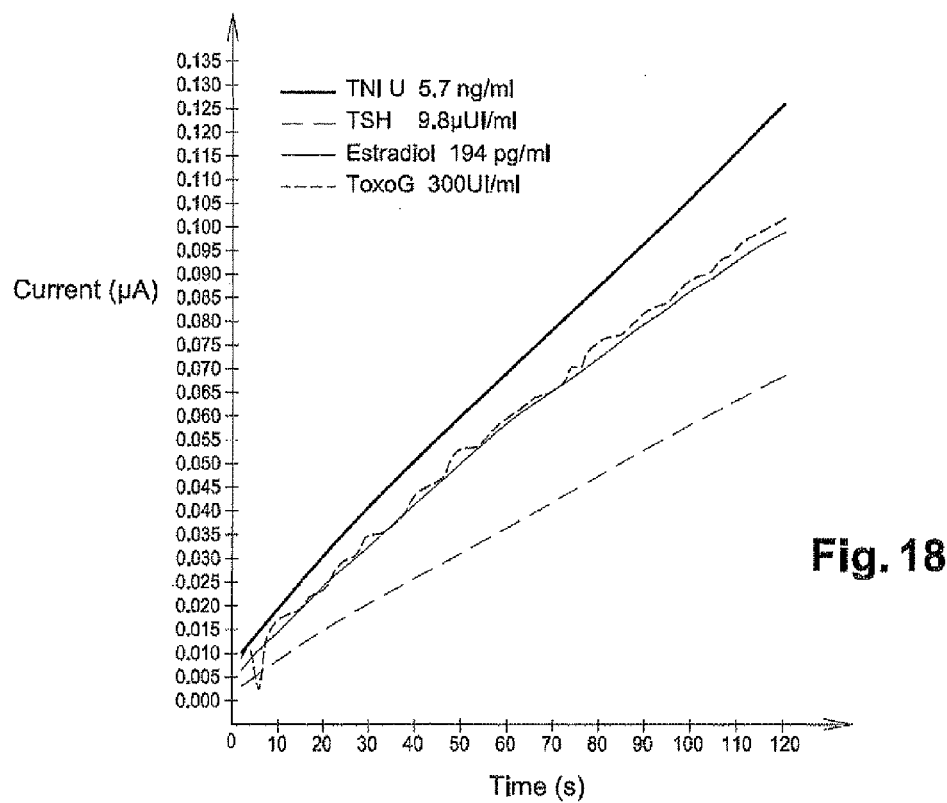
FIG. 18 is a curve relating to the second example showing the variation of a current measured as a function of time.

The four assays are started simultaneously on apparatus for analysis. The four assay protocols vary in their number of stages and the duration of these various stages, which is between 10 and 19 min. After passage of the last reagent—the PAPP enzyme substrate—electrochemical detection is initiated in each of the channels as described in example 1. The variation of the current as a function of time is measured and is shown in FIG. 18.

After establishing calibration curves, it is possible, from measurement of the slopes at the origin, to determine the dose of each of the four analytes in the four samples tested, which may or may not be from the same patient.

Example 3

Reproducibility of 4 Simultaneous Assays on Samples of Whole Blood

Figure 19:
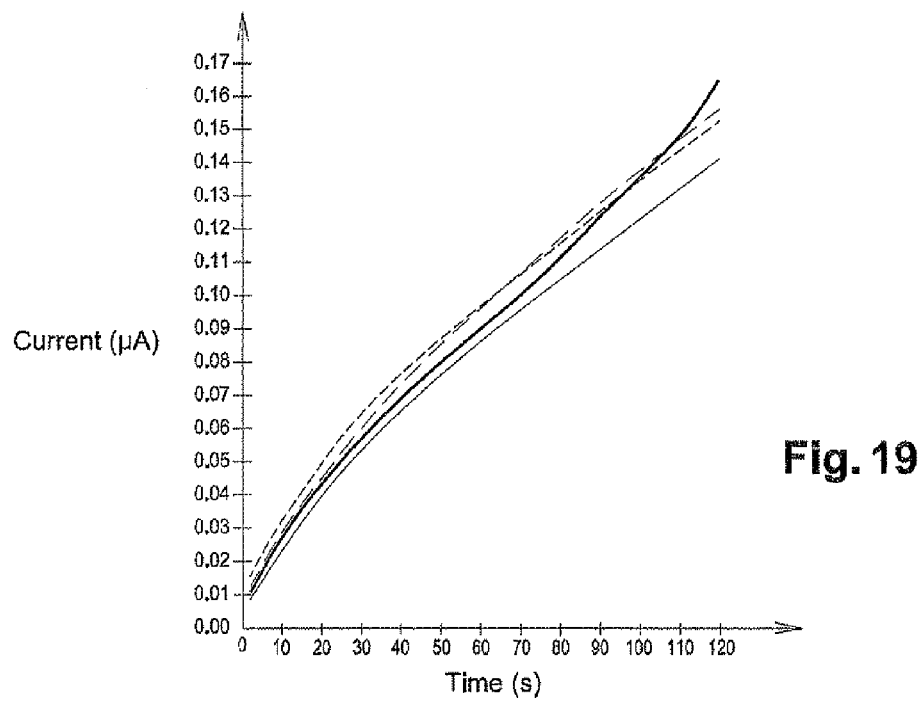
FIG. 19 is a curve relating to the third example showing the variation of a current measured as a function of time.

Four channels are functionalized with anti-troponin antibodies. These four channels are glued under four separate bases, equipped in their turn with four drawers. Each of these drawers is filled with the specific troponin reagents as described in example 1. One and the same sample of whole blood is tested four times on each of the four channels. The assays are started simultaneously on the four stations of an apparatus for analysis, followed by electrochemical detection. The slopes of the curves of intensity as a function of time obtained for each of the channels are measured. The reproducibility (CV) of the four assays can thus be measured as shown in FIG. 19 and referring to the following Table II.

| Station | Slope (A/s) |
| --- | --- |
| 1 | 1.47E−09 |
| 2 | 1.62E−09 |
| 3 | 1.43E−09 |
| 4 | 1.57E−09 |
| Mean | 1.52E−09 |
| CV (%) | 5.76% |

Example 4

Limit of Analytical Detection of the Troponin Parameter

The 32 channels of 32 chips are functionalized with anti-troponin antibodies. These various channels 21 are tested as described previously for the parameter Troponin, in the presence of calibration samples of known troponin concentration. 20 tests are performed in the presence of serum with zero or nondetectable troponin concentration. 12 tests are performed in the presence of serum with low troponin concentration (0.2 ng/ml). The limit of detection is evaluated at twice the standard deviation for all of the negative tests, i.e. a value of 0.023 ng/ml.

Although the invention has been described in connection with particular examples of embodiments, obviously it is not limited to these and includes all the technical equivalents of the means described as well as their combinations if the latter fall within the scope of the invention.

The invention claimed is:

1. A device for at least one of preparation, treatment and analysis of a biological sample comprising:
a base;
a microfluidic chip mounted or formed on the base, the microfluidic chip including fluidic channel; and
a drawer including a set of at least one of storage and reaction chambers intended to receive a fluid, said chambers being separated by walls to constitute a set of adjacent chambers,
said drawer further including a contact surface onto which a first means for establishing fluid communication opens, the first means for establishing fluid communication being connected to an internal volume of one or more of said chambers, the contact surface of the drawer being configured to be positioned opposite a contact surface of the base, the contact surface of the base having at least one position at which a second fluid communication means is arranged in fluid communication with the microfluidic chip,
wherein the drawer is movable in translation relative to the base to selectively place different chambers in fluid communication with the microfluidic chip through the first and second fluid communication means.

2. The device as claimed in claim 1, in which at least one seal is provided on the contact surface of the drawer.

3. The device as claimed in claim 1, in which the microfluidic chip further includes a reaction chamber, and at least one of the fluidic channel and the reaction chamber is connected to the second fluid communication means.

4. The device as claimed in claim 1, in which the first fluid communication means comprises at least one opening made in the drawer and opening onto the contact surface of the drawer.

5. The device as claimed in claim 4, further comprising sealing means that include at least one seal positioned around the opening.

6. The device as claimed in claim 5, in which the sealing means comprise two concentric seals, positioned around the opening.

7. The device as claimed in claim 1, further comprising wipers positioned between the contact surface of the drawer and the contact surface of the base.

8. The device as claimed in claim 1, further comprising mechanical means for positioning the microfluidic chip on the base.

9. The device as claimed in claim 8, in which the mechanical means comprises at least one pin and an opening of complementary shape.

10. The device as claimed in claim 1, in which the drawer comprises two parts constituted of two different materials, one of the two parts comprising a material that is more rigid than a material of a second part of the two parts, the second part having the first fluid communication means.

11. The device as claimed in claim 1, in which the drawer comprises a separate set of positioning stops or notches depending on a direction of movement of the drawer relative to the base.

12. The device as claimed in claim 1, in which the microfluidic chip and the base are formed as a single piece, an upper face of the microfluidic chip at least partly constituting the contact surface of the base.

13. An apparatus for analysis comprising:
a device as claimed in claim 1;
a treatment station;
driving means at the treatment station for relative movement of the drawer relative to the base; and
transferring means arranged for transferring an amount of fluid to the at least one of the storage and reaction chambers of the drawer or from the at least one of the storage and reaction chambers of the drawer via the first fluid communication means.

14. The apparatus as claimed in claim 13, further comprising, at the treatment station, electrical connection means comprising at least one conducting tab intended for establishing an electrical connection with a contact of the microfluidic chip of the device in which at least one of the fluidic channel and a reaction chamber of the microfluidic chip is connected to the second fluid communication means.

15. The apparatus as claimed in claim 13, further comprising a storage station configured to receive and store a set of devices in columns and rows.

16. The apparatus as claimed in claim 13, further comprising a station of chambers for filling the drawer with reagents, liquids or samples.

17. The apparatus as claimed in claim 16, further comprising,
- a filling station; and
- at least one pipet or a needle for filling the at least one of the storage and reaction chambers of the drawer at the filling station, the pipet or needle being movable between a first high position and a second low position,
- said needle or pipet being connected to a reservoir of reagent or some other liquid, or to a container of a sample to be analyzed.

18. The apparatus as claimed in claim 13, further comprising a conveying or manipulating mechanism enabling the device to be moved between stations of the apparatus.

19. A device for at least one of preparation, treatment and analysis of a biological sample comprising:
- a base comprising housing;
- a microfluidic chip mounted or formed on the base, the microfluidic chip including a fluidic channel; and
- a drawer movable in translation relative to the base, the housing of the base having a section that is configured to guide the movement of the drawer,
- the drawer including a set of at least one of storage and reaction chambers intended to receive a fluid, said chambers being separated by walls to constitute a set of adjacent chambers,
- said drawer further including a contact surface onto which a first means for establishing fluid communication opens, the first means for establishing fluid communication being connected to an internal volume of one or more of said chambers, the contact surface of the drawer being configured to be positioned opposite a contact surface of the base, the contact surface of the base having at least one position at which a second fluid communication means is arranged in fluid communication with the microfluidic chip.

20. The device as claimed in claim 19, in which dimensions of the drawer are greater than dimensions of the housing, to create a stress when the drawer is received in the housing and to keep the contact surface of the drawer in contact with the contact surface of the base.

21. A device for preparing, treating, or analyzing a biological sample, comprising:
- a base including a contact surface having at least one fluid communication opening;
- a drawer including a contact surface and a plurality of chambers separated by walls, the contact surface having fluid communication openings and individual chambers being a storage or reaction chamber; and
- a microfluidic chip mounted or formed on the base, the microfluidic chip including a fluidic channel,
- wherein the contact surface of the drawer is movable in translation relative to the contact surface of the base to selectively place different chambers in fluid communication with the microfluidic chip.

* * * * *